US012674794B2

(12) United States Patent
Liu et al.

(10) Patent No.: US 12,674,794 B2
(45) Date of Patent: Jul. 7, 2026

(54) METHOD AND SYSTEM FOR QUANTITATIVELY EVALUATING KEROGEN SWELLING OIL IN SHALE

(71) Applicant: Northeast Petroleum University, Daqing (CN)

(72) Inventors: Bo Liu, Daqing (CN); Shansi Tian, Daqing (CN); Fang Zeng, Daqing (CN); Xiaofei Fu, Daqing (CN); Boyang Wang, Daqing (CN); Longhui Bai, Daqing (CN); Haiyang Yan, Daqing (CN)

(73) Assignee: Northeast Petroleum University, Daqing (CN)

( * ) Notice: Subject to any disclaimer, the term of this patent is extended or adjusted under 35 U.S.C. 154(b) by 1528 days.

(21) Appl. No.: 17/024,223

(22) Filed: Sep. 17, 2020

(65) Prior Publication Data

US 2022/0058303 A1     Feb. 24, 2022

(30) Foreign Application Priority Data

Aug. 24, 2020    (CN) .......................... 202010856536.9

(51) Int. Cl.
| | |
|---|---|
| *G16C 10/00* | (2019.01) |
| *C10G 1/00* | (2006.01) |
| *G01N 33/24* | (2006.01) |
| *G16C 20/30* | (2019.01) |

(52) U.S. Cl.
CPC ............. *G01N 33/241* (2013.01); *C10G 1/00* (2013.01); *G16C 10/00* (2019.02); *G16C 20/30* (2019.02)

(58) Field of Classification Search
None
See application file for complete search history.

(56) References Cited

U.S. PATENT DOCUMENTS

2022/0059191 A1* 2/2022 Tian ....................... G16C 60/00

OTHER PUBLICATIONS

Yang, Yongfei, et al. "Adsorption behaviors of shale oil in kerogen slit by molecular simulation." Chemical Engineering Journal 387 (2020): 124054. (Year: 2020).*
Hao Yu, HengYu Xu, JingCun Fan, FengChao Wang, and HengAn Wu. The Journal of Physical Chemistry C 2020 124 (23), 12752-12765 (Year: 2020).*
Pang, Yu, Yongming He, and Shengnan Chen. "An innovative method to characterize sorption-induced kerogen swelling in organic-rich shales." Fuel 254 (2019): 115629. (Year: 2019).*
Van Der Spoel, D., Lindahl, E., Hess, B., Groenhof, G., Mark, A.E. and Berendsen, H.J.C. (2005), GROMACS: Fast, flexible, and free. J. Comput. Chem., 26: 1701-1718. (Year: 2005).*
Fei, Junsheng, et al. "Molecular dynamics simulation of adsorption and absorption behavior of shale oil in realistic kerogen slits." Energy & Fuels 37.5 (2023): 3654-3671 (Year: 2023).*
Zhang, Yiqun, et al. "Insight into adsorption behaviors of shale oil in kerogen slit by molecular dynamics." Fuel 374 (2024): 132432. (Year: 2024).*
Zheng, Yijun, Chunqing Jiang, and Yuhong Liao. "Relationship between hydrocarbon gas generation and kerogen structural evolution revealed by closed system pyrolysis and quantitative Py-GC analysis of a type II kerogen." Energy & Fuels 35.1 (2020): 251-263 (Year: 2020).*

* cited by examiner

*Primary Examiner* — Kaitlyn L Minchella
*Assistant Examiner* — Jonathan Edward Hayes
(74) *Attorney, Agent, or Firm* — MARSHALL, GERSTEIN & BORUN LLP

(57)     ABSTRACT

A method and system for quantitatively evaluating kerogen swelling oil in shale is provided. The method includes: establishing different types of kerogen molecular models, and loading each of the kerogen molecular models into a graphene slit-type pore composed of a lamellar structure; performing energy minimization (EM), relaxation and annealing to obtain a kerogen slit-type pore; loading a shale oil molecule into the kerogen slit-type pore to obtain an initial model of swelling and adsorption of shale oil in kerogen; assigning a value to a force field of the shale oil molecule and the kerogen molecule in the swelling and adsorption model to obtain a density of the kerogen and the shale oil; plotting a density curve of the kerogen and the shale oil; calculating kerogen swelling oil mass; determining per-unit kerogen swelling oil mass; and determining the kerogen swelling oil mass in different evolution stages.

2 Claims, 5 Drawing Sheets

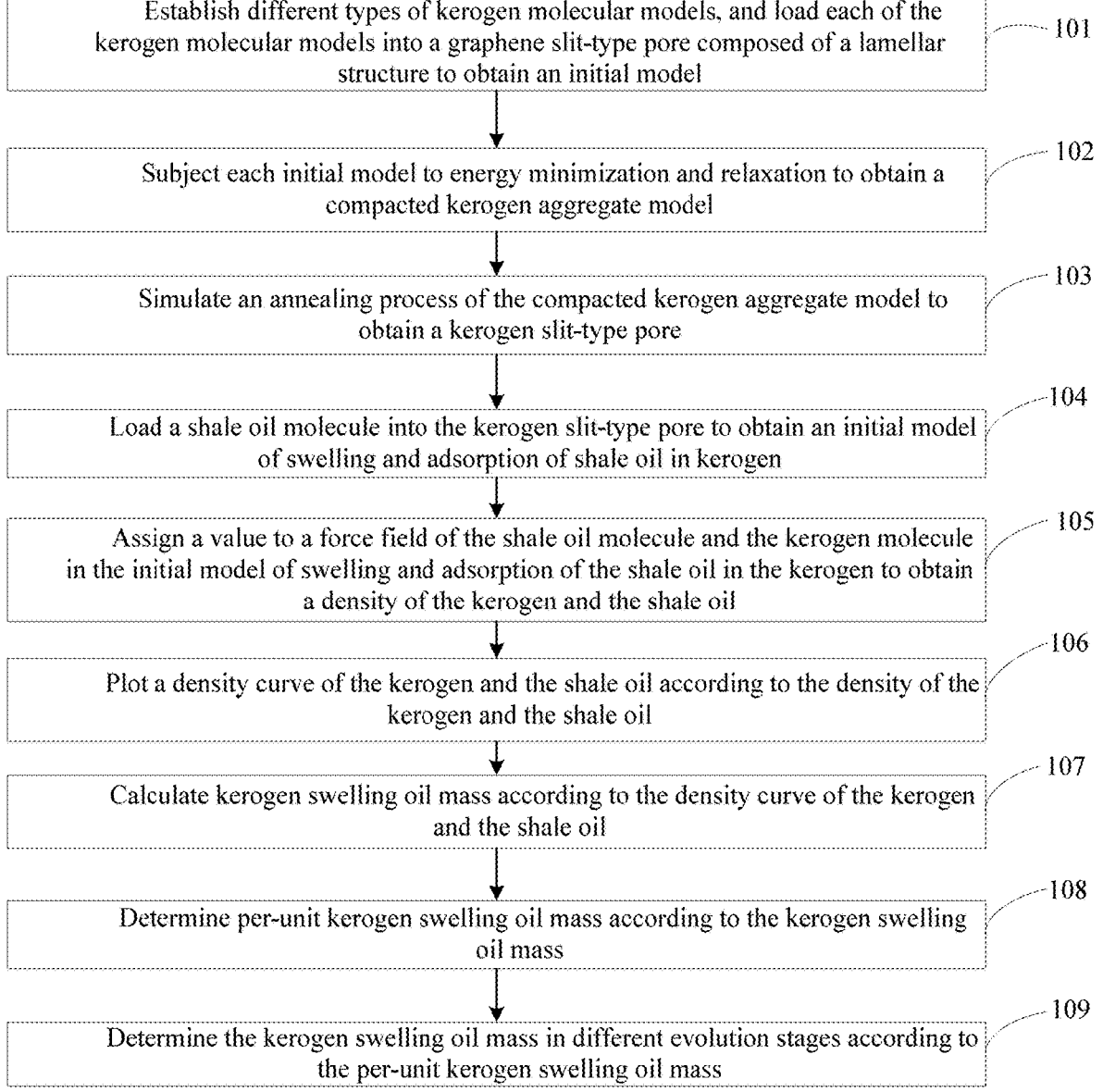

Establish different types of kerogen molecular models, and load each of the kerogen molecular models into a graphene slit-type pore composed of a lamellar structure to obtain an initial model — 101

Subject each initial model to energy minimization and relaxation to obtain a compacted kerogen aggregate model — 102

Simulate an annealing process of the compacted kerogen aggregate model to obtain a kerogen slit-type pore — 103

Load a shale oil molecule into the kerogen slit-type pore to obtain an initial model of swelling and adsorption of shale oil in kerogen — 104

Assign a value to a force field of the shale oil molecule and the kerogen molecule in the initial model of swelling and adsorption of the shale oil in the kerogen to obtain a density of the kerogen and the shale oil — 105

Plot a density curve of the kerogen and the shale oil according to the density of the kerogen and the shale oil — 106

Calculate kerogen swelling oil mass according to the density curve of the kerogen and the shale oil — 107

Determine per-unit kerogen swelling oil mass according to the kerogen swelling oil mass — 108

Determine the kerogen swelling oil mass in different evolution stages according to the per-unit kerogen swelling oil mass — 109

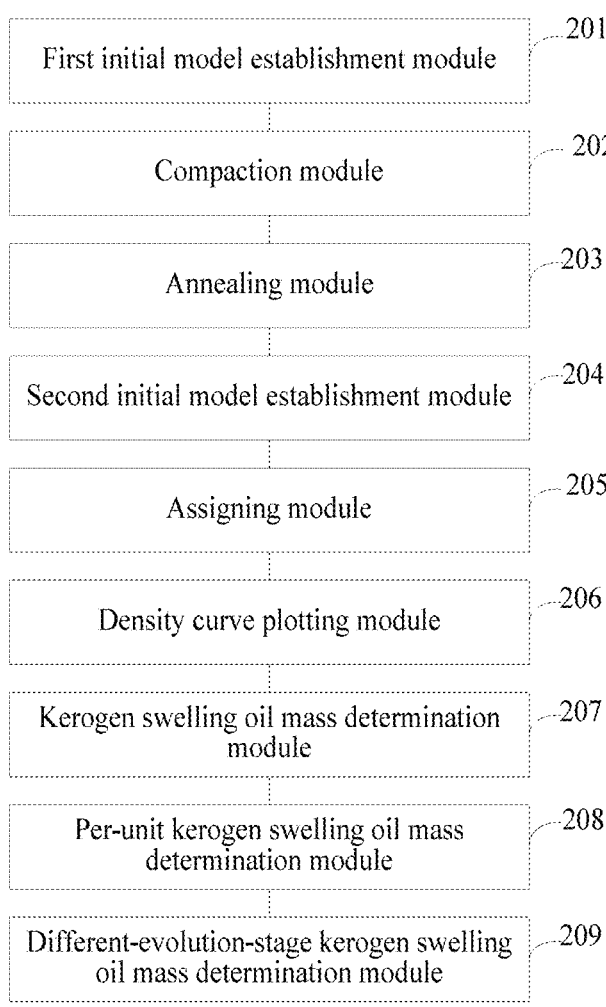

First initial model establishment module ⟋201

Compaction module ⟋202

Annealing module ⟋203

Second initial model establishment module ⟋204

Assigning module ⟋205

Density curve plotting module ⟋206

Kerogen swelling oil mass determination module ⟋207

Per-unit kerogen swelling oil mass determination module ⟋208

Different-evolution-stage kerogen swelling oil mass determination module ⟋209

FIG. 7

METHOD AND SYSTEM FOR QUANTITATIVELY EVALUATING KEROGEN SWELLING OIL IN SHALE

TECHNICAL FIELD

The present invention relates to the field of quantitative evaluation of kerogen swelling oil, and in particular, to a method and system for quantitatively evaluating kerogen swelling oil in shale.

BACKGROUND

The effective exploration and development of shale oil in the United States and fractured shale reservoirs in China indicate that shale has the potential to become an oil reservoir. The effective mobility and flow of oil in the shale are related to the size, structure, distribution and connectivity of the pore throat of the shale, as well as the liquid-solid interactions and the occurrence states (such as adsorbed, free and dissolved) and mechanisms of oil in the reservoirs. Therefore, the effective mobility and flow of shale oil are further related to the composition, types and physical properties of the shale oil, such as viscosity and density.

Preliminary evaluation shows that China's shale oil resources are very rich, and the geological resources reach 32 billion barrels, ranking third among 41 countries in the world (total 345 billion barrels in the world). At present, China has discovered a batch of geological resources of $5 \times 10^8$ tons to $10 \times 10^8$ tons in the Triassic Yanchang Formation of the Ordos Basin, the Permian Lucaogou Formation of the Junggar Basin and the Qing-1 Member of the Songliao Basin. There are also many important geological resources discovered in the gray shale in the Bohai Bay and the Sichuan Basin. Compared with the marine shale oil in the North America, China's lacustrine shale oil is heavier, with higher wax content and higher polar components (colloid and asphaltene) than the North American shale oil. These heavy components interact strongly with kerogen and nanopores that are widely developed in the minerals of shale, making lacustrine shale oil more adsorbable in shale reservoirs and difficult to be effectively developed. These polar components lead to errors of recoverable resource estimation and thus should be considered in the evaluation of shale oil resources.

Molecular dynamics methods have been greatly expanded in terms of theory, technology and application since their establishment. They are applied to equilibrium and non-equilibrium systems. Due to the complexity of kerogen (with complex elements and functional groups), graphene is usually used instead of kerogen to conduct the molecular dynamics simulation of the interaction of shale oil on the surface of kerogen. However, since graphene is a two-dimensional simple carbon material, it is not feasible to be used instead of kerogen to study the adsorption of shale oil. In addition, the shale oil adsorption system used for the molecular dynamics simulation is usually less than 20 nm, while the pore size of most shale reservoirs is greater than 20 nm. Therefore, it is difficult to apply such a small adsorption system to the swelling shale oil.

SUMMARY

An objective of the present invention is to provide a method and system for quantitatively evaluating kerogen swelling oil in shale. The present invention improves the accuracy of the quantitative evaluation of the kerogen swelling oil.

To achieve the above purpose, the present invention provides the following technical solutions.

A method for quantitatively evaluating kerogen swelling oil in shale includes:

establishing different types of kerogen molecular models, and loading each of the kerogen molecular models into a graphene slit-type pore composed of a lamellar structure to obtain an initial model;

subjecting each initial model to energy minimization (EM) and relaxation to obtain a compacted kerogen aggregate model;

simulating an annealing process of the compacted kerogen aggregate model to obtain a kerogen slit-type pore;

loading a shale oil molecule into the kerogen slit-type pore to obtain an initial model of swelling and adsorption of shale oil in kerogen;

assigning a value to a force field of the shale oil molecule and the kerogen molecule in the initial model of swelling and adsorption of the shale oil in the kerogen to obtain a density of the kerogen and the shale oil;

plotting a density curve of the kerogen and the shale oil according to the density of the kerogen and the shale oil;

calculating kerogen swelling oil mass according to the density curve of the kerogen and the shale oil;

determining per-unit kerogen swelling oil mass according to the kerogen swelling oil mass; and determining the kerogen swelling oil mass in different evolution stages according to the per-unit kerogen swelling oil mass.

Optionally, the subjecting each initial model to EM and relaxation to obtain a compacted kerogen aggregate model specifically includes:

subjecting the initial model to EM and 200 ps relaxation at 75° C. under 20 MPa by using Gromacs software to obtain a compacted kerogen aggregate model.

Optionally, the simulating an annealing process of the compacted kerogen aggregate model to obtain a kerogen slit-type pore specifically includes:

subjecting the compacted kerogen aggregate model to 200 ps relaxation for warming; and subjecting the kerogen aggregate model after the relaxation warming to 2 ns simulation, cooling and pressurization by using an isothermal-isobaric ensemble (NPT ensemble) at 800° C. under normal pressure to obtain a kerogen slit-type pore.

Optionally, the calculating kerogen swelling oil mass according to the density curve of the kerogen and the shale oil specifically includes:

calculating the kerogen swelling oil mass by $$Q_{oil} = \int_{L_{o1}}^{L_{o2}} S_{model} \cdot \rho_{oil} dL$$

according to the density curve of the kerogen and the shale oil;

where, $Q_{oil}$ is the kerogen swelling oil mass; $L_{o1}$ is a start position of an intersection between the kerogen density curve and the shale oil density curve; $L_{o2}$ is a stop position of the intersection between the kerogen density curve and the shale oil density curve; $S_{model}$ is a cross-sectional area of the swelling and adsorption model of the shale oil in the kerogen; $\rho_{oil}$ is the shale oil density curve.

Optionally, the determining per-unit kerogen swelling oil mass according to the kerogen swelling oil mass specifically includes:

deriving the mass of the kerogen; and determining the per-unit kerogen swelling oil mass according to the kerogen adsorbed oil mass and the kerogen mass.

Optionally, the determining the kerogen swelling oil mass in different evolution stages according to the per-unit kerogen swelling oil mass specifically includes:

deriving the mass of the kerogen in different evolution stages;

calculating the kerogen swelling oil mass in different evolution stages by $Q_s=Q_w \cdot m_k \cdot f_s$ according to the per-unit kerogen swelling oil mass and the kerogen mass in different evolution stages;

where, $Q_w$ is the kerogen swelling oil mass; $m_k$ is the kerogen mass in different evolution stages; $f_s$ is a swelling ratio reduction coefficient in different evolution stages.

A system for quantitatively evaluating kerogen swelling oil in shale includes:

a first initial model establishment module, for establishing different types of kerogen molecular models, and loading each of the kerogen molecular models into a graphene slit-type pore composed of a lamellar structure to obtain an initial model;

a compaction model, for subjecting each initial model to EM and relaxation to obtain a compacted kerogen aggregate model;

an annealing model, for simulating an annealing process of the compacted kerogen aggregate model to obtain a kerogen slit-type pore;

a second initial model establishment module, for loading a shale oil molecule into the kerogen slit-type pore to obtain an initial model of swelling and adsorption of shale oil in kerogen;

an assigning module, for assigning a value to a force field of the shale oil molecule and the kerogen molecule in the initial model of swelling and adsorption of the shale oil in the kerogen to obtain a density of the kerogen and the shale oil;

a density curve plotting module, for plotting a density curve of the kerogen and the shale oil according to the density of the kerogen and the shale oil;

a kerogen swelling oil mass determination module, for deriving the kerogen swelling oil mass according to the density curve of the kerogen and the shale oil;

a per-unit kerogen swelling oil mass determination module, for determining per-unit kerogen swelling oil mass according to the kerogen swelling oil mass; and a different-evolution-stage kerogen swelling oil mass determination module, for determining the kerogen swelling oil mass in different evolution stages according to the per-unit kerogen swelling oil mass.

Optionally, the compaction module specifically includes: a compaction unit, for subjecting the initial model to EM and 200 ps relaxation at 75° C. under 20 MPa by using Gromacs software to obtain a compacted kerogen aggregate model.

Optionally, the annealing module specifically includes: a warming unit, for subjecting the compacted kerogen aggregate model to 200 ps relaxation for warming; and

an annealing unit, for subjecting the kerogen aggregate model after the relaxation warming to 2 ns simulation, cooling and pressurization by using a NPT ensemble at 800° C. under normal pressure to obtain a kerogen slit-type pore.

Optionally, the kerogen swelling oil mass determination module specifically includes:

a kerogen swelling oil mass determination unit, for deriving the kerogen swelling oil mass by $$Q_{oil} = \int_{L_{o1}}^{L_{o2}} S_{model} \cdot \rho_{oil} dL$$

according to the density curve of the kerogen and the shale oil;

where, $Q_{oil}$ is the kerogen swelling oil mass; $L_{o1}$ is a start position of an intersection between the kerogen density curve and the shale oil density curve; $L_{o2}$ is a stop position of the intersection between the kerogen density curve and the shale oil density curve; $S_{model}$ is a cross-sectional area of the swelling and adsorption model of the shale oil in the kerogen; $\rho_{oil}$ is the shale oil density curve.

According to the specific examples provided by the present invention, the present invention discloses the following technical effects.

The present invention uses a real kerogen model, which overcomes the problems caused by the conventional method of using simple graphene instead of kerogen to study the kerogen-shale oil interaction. As graphene is a two-dimensional carbon material with a smooth surface and a surface structure different from kerogen molecules, shale oil molecules cannot pass through the graphene and enter its lamellar structure to make the graphene swell like the real kerogen structure. A kerogen aggregate model is preprocessed to prevent incomplete compaction of a kerogen aggregate. If the kerogen aggregate is incompletely compacted, it will result in the existence of "large pores" inside, making the density of the kerogen aggregate model lower than that of a kerogen sample. In the present invention, the processing of per-unit kerogen swelling oil mass overcomes the problem that a molecular dynamics simulation system is too small to be applied to the swelling shale oil. A shale oil-kerogen system used for molecular dynamics simulation is usually less than 20 nm, while the pore size of most shale reservoirs is greater than 20 nm. The present invention calculates the per-unit kerogen swelling oil mass, and calculates the actual kerogen swelling oil mass based on actual geological parameters such as swelling coefficient reduction and kerogen mass change, which greatly improves the accuracy of the results.

BRIEF DESCRIPTION OF DRAWINGS

In order to describe the technical solutions in the examples of the present invention or in the prior art more clearly, the accompanying drawings required for the examples are briefly described below. Apparently, the accompanying drawings in the following description show merely some examples of the present invention, and a person of ordinary skill in the art may still derive other accompanying drawings from these accompanying drawings without creative efforts.

FIG. 1 is a flowchart of a method for quantitatively evaluating kerogen swelling oil in shale according to the present invention.

FIG. 7 is a structural diagram of a system for quantitatively evaluating kerogen swelling oil in shale according to the present invention.

DETAILED DESCRIPTION

The technical solutions in the examples of the present invention are clearly and completely described with reference to the accompanying drawings in the examples of the present invention. Apparently, the described examples are merely a part rather than all of the examples of the present invention. All other examples obtained by a person of ordinary skill in the art based on the examples of the present invention without creative efforts should fall within the protection scope of the present invention.

An objective of the present invention is to provide a method and system for quantitatively evaluating kerogen swelling oil in shale. The present invention improves the accuracy of the quantitative evaluation of the kerogen swelling oil.

In order to make the above objectives, features, and advantages of the present invention clearer and more comprehensible, the present invention is described in further detail below with reference to the accompanying drawings and specific implementations.

FIG. 1 is a flowchart of a method for quantitatively evaluating kerogen swelling oil in shale according to the present invention. As shown FIG. 1, a method for quantitatively evaluating kerogen swelling oil in shale includes:

Step 101: establish different types of kerogen molecular models, and load each of the kerogen molecular models into a graphene slit-type pore composed of a lamellar structure to obtain an initial model.

Avogadro software was used to establish type I, II and III kerogen molecular models. As a preferred example, only the type II kerogen molecular model is used for illustration. Specifically, Packmol software was used to load 100 type II kerogen molecules into the graphene slit-type pore composed of a lamellar structure (approximately 7.38 nm×7.67 nm×0.85 nm). FIG. 2a shows an initial kerogen wall model.

Step 102: subject each initial model to energy minimization (EM) and relaxation to obtain a compacted kerogen aggregate model, specifically as follows:

Subject the initial model to EM and 200 ps relaxation at 75° C. under 20 MPa by using an isothermal-isobaric ensemble (NPT ensemble) of Gromacs software to obtain a compacted kerogen aggregate model.

Figure 2:
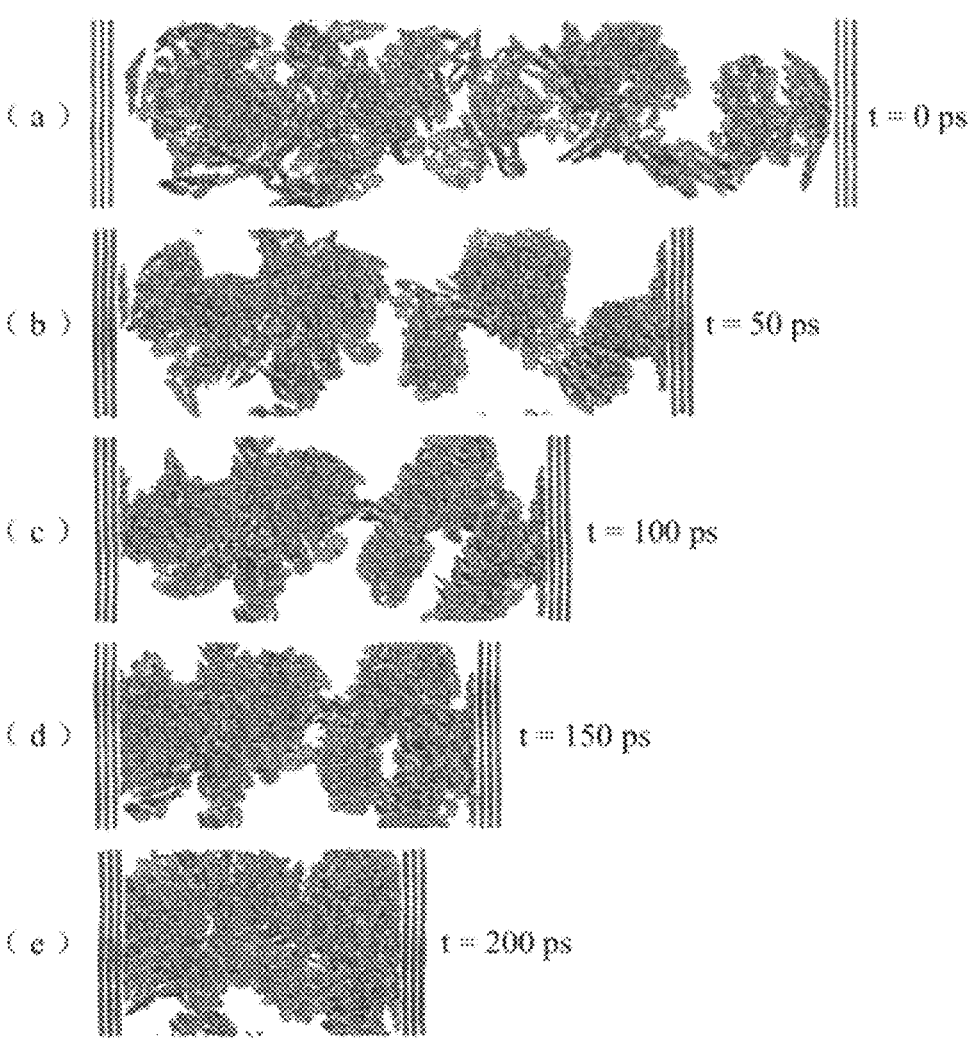
FIG. 2 shows a process of establishing a kerogen wall model according to the present invention.

FIG. 2 shows a process of establishing a kerogen wall model according to the present invention, where a shows an initial model, b shows a model after 50 ps relaxation, c shows a model after 100 ps relaxation, d shows a model after 150 ps relaxation, and e shows a model after 200 ps relaxation.

Step 103: simulate an annealing process of the compacted kerogen aggregate model to obtain a kerogen slit-type pore, specifically as follows:

Subject the compacted kerogen aggregate model to 200 ps relaxation for warming.

Subject the kerogen aggregate model after the relaxation warming to 2 ns simulation, cooling and pressurization by using the NPT ensemble at 800° C. under normal pressure to obtain a kerogen slit-type pore.

Figure 3:
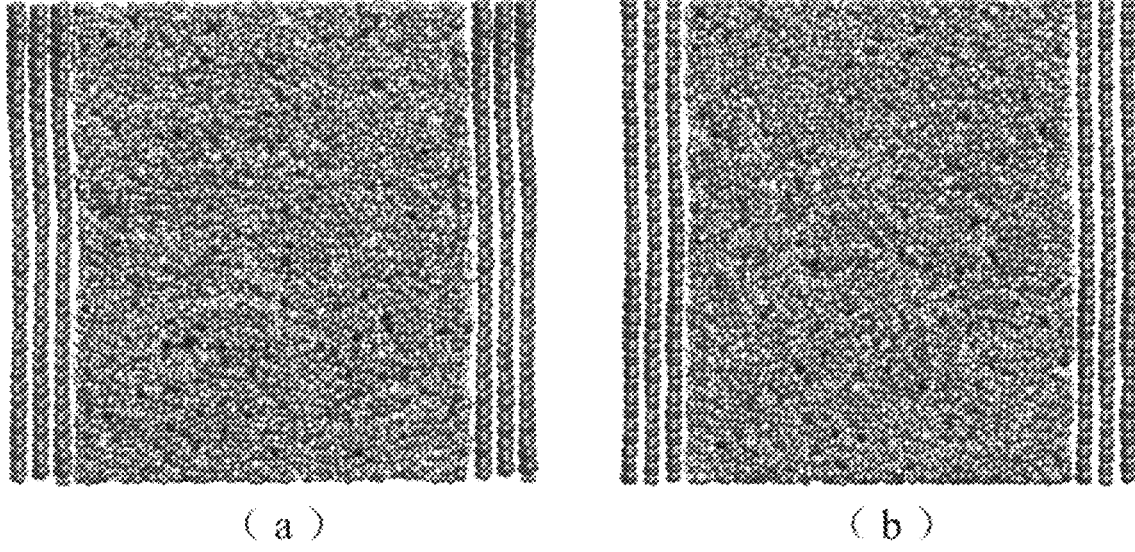
FIG. 3 shows a simulation of an annealing process of a kerogen aggregate model according to the present invention.

FIG. 3 shows a simulation of an annealing process of a kerogen aggregate model according to the present invention, where, a shows a result after 2 ns simulation at 800° C. under normal pressure, and b shows a result after 2 ns simulation at 75° C. under 20 MPa. In this step, the compacted kerogen aggregate model was warmed by 200 ps relaxation, and the system was reduced to normal pressure. Then the entire system was simulated by using the NPT ensemble at 800° C. under normal pressure for 2 ns. FIG. 3a shows a final frame of the simulation. Then the system was cooled and pressurized. The entire system was simulated by using the NPT ensemble at 75° C. under 20 MPa for 2 ns. FIG. 3b shows a final frame of the simulation.

Step 104: load a shale oil molecule into the kerogen slit-type pore to obtain an initial model of swelling and adsorption of shale oil in kerogen.

Figure 4:
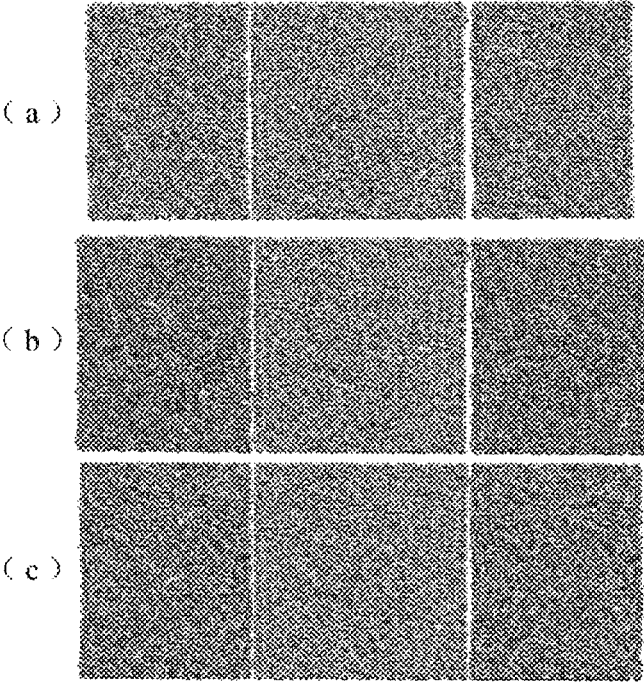
FIG. 4 shows an initial model of swelling and adsorption of shale oil in different types of kerogen according to the present invention.

Packmol software was used to load the shale oil molecule into the kerogen slit-type pore obtained in step 103. FIG. 4 shows an initial model after loading, where the model is composed of a kerogen wall model (after the annealing process simulated) on double sides and a shale oil model in the middle.

FIG. 4 shows an initial model of swelling and adsorption of shale oil in different types of kerogen. In the figure, a shows a swelling and adsorption model of shale oil in type I kerogen, b shows a swelling and adsorption model of shale oil in type II kerogen, and c shows a swelling and adsorption model of shale oil in type III kerogen.

Step 105: assign a value to a force field of the shale oil molecule and the kerogen molecule in the initial model of swelling and adsorption of the shale oil in the kerogen to obtain a density of the kerogen and the shale oil.

Figure 5:
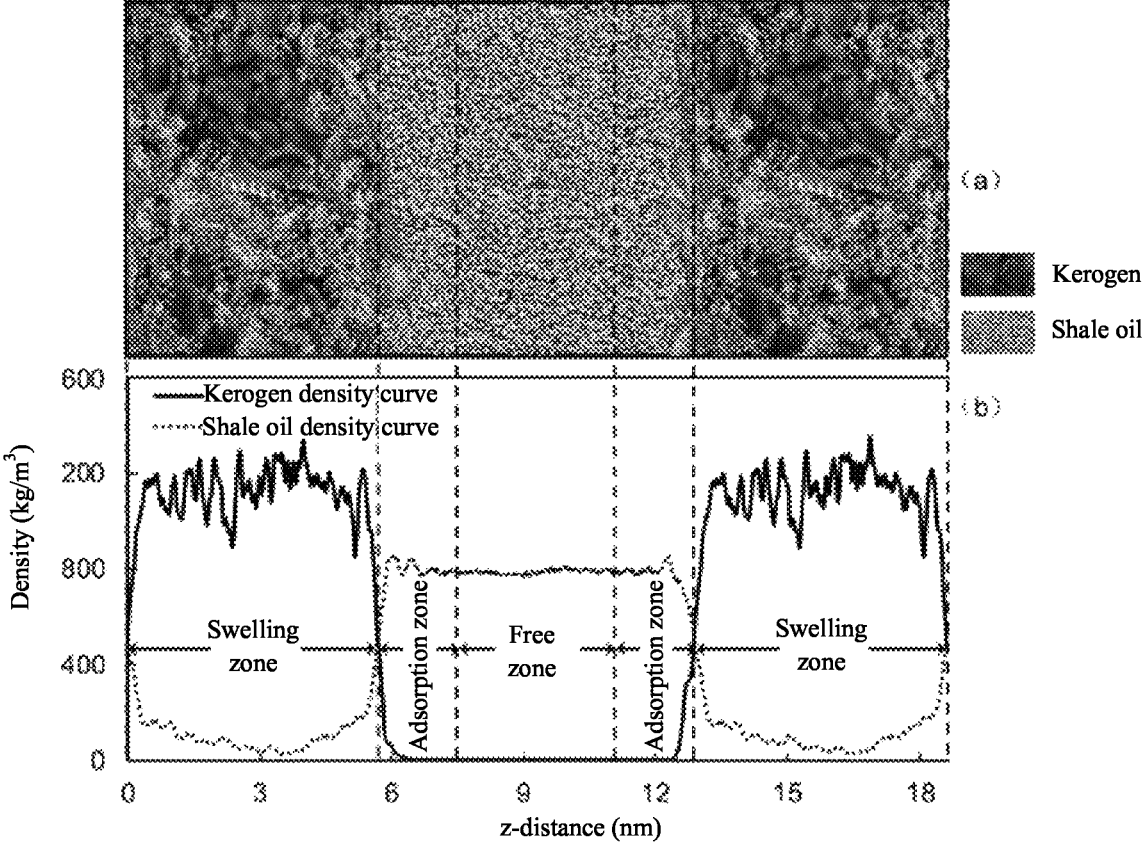
FIG. 5 shows a molecular dynamics simulation of swelling and adsorption in type II kerogen according to the present invention.

FIG. 5 shows a molecular dynamics simulation of swelling and adsorption in type II kerogen, where a shows a final frame of the simulation, and b shows a density curve of the kerogen and the shale oil. The Chemistry at Harvard Macromolecular Mechanics (CHARMM) 36/CHARMM general (CGenFF) force field was used to assign a value to the force field of the shale oil molecule and the kerogen molecule in the initial model of swelling and adsorption of the shale oil in the kerogen obtained in step 104. The Lorentz-Berthelot (LB) mixing rule was used to calculate an interaction force between the shale oil molecule and the kerogen molecule. The Particle-Mesh-Ewald (PME) model was used as an electrostatic force model. The van der Waals radius was 1.4 nm. The model after the force field assignment was simulated by using the NPT ensemble of Gromacs software at 75° C. under 20 MPa for 200 ns. Taking type II kerogen as an example, the simulation result is shown in FIG. 5a. The density curves of the kerogen and the shale oil were plotted (step 106), as shown in FIG. 5b.

Step 106: plot a density curve of the kerogen and the shale oil according to the density of the kerogen and the shale oil.

Step 107: derive the kerogen swelling oil mass according to the density curve of the kerogen and the shale oil, specifically as follows:

calculate the kerogen swelling oil mass by $$Q_{oil} = \int_{L_{o1}}^{L_{o2}} S_{model} \cdot \rho_{oil} dL$$

according to the density curve of the kerogen and the shale oil.

In the formula, $Q_{oil}$ is the kerogen swelling oil mass; $L_{o1}$ is a start position of an intersection between the kerogen density curve and the shale oil density curve; $L_{o2}$ is a stop position of the intersection between the kerogen density curve and the shale oil density curve; $S_{model}$ is a cross-sectional area of the swelling and adsorption model of the shale oil in the kerogen; $\rho_{oil}$ is the shale oil density curve.

Step 108: determine per-unit kerogen swelling oil mass according to the kerogen swelling oil mass, specifically as follows:

derive the mass of the kerogen; and determine the per-unit kerogen swelling oil mass according to the kerogen adsorbed oil mass and the kerogen mass.

The swelling oil mass in the type I kerogen, the swelling oil mass in the type II kerogen and the swelling oil mass in the type III kerogen were 161.04 mg/g TOC, 104.96 mg/g TOC and 70.29 mg/g TOC, respectively.

Step 109: determine the kerogen swelling oil mass in different evolution stages according to the per-unit kerogen swelling oil mass, specifically as follows:

derive the mass of the kerogen in different evolution stages; and calculate the kerogen swelling oil mass in different evolution stages by $Q_s=Q_w\cdot m_k\cdot f_s$ according to the per-unit kerogen swelling oil mass and the kerogen mass in different evolution stages.

In the formula, $Q_w$ is the kerogen swelling oil mass; $m_k$ is the kerogen mass in different evolution stages; $f_s$ is a swelling ratio reduction coefficient in different evolution stages.

Figure 6:
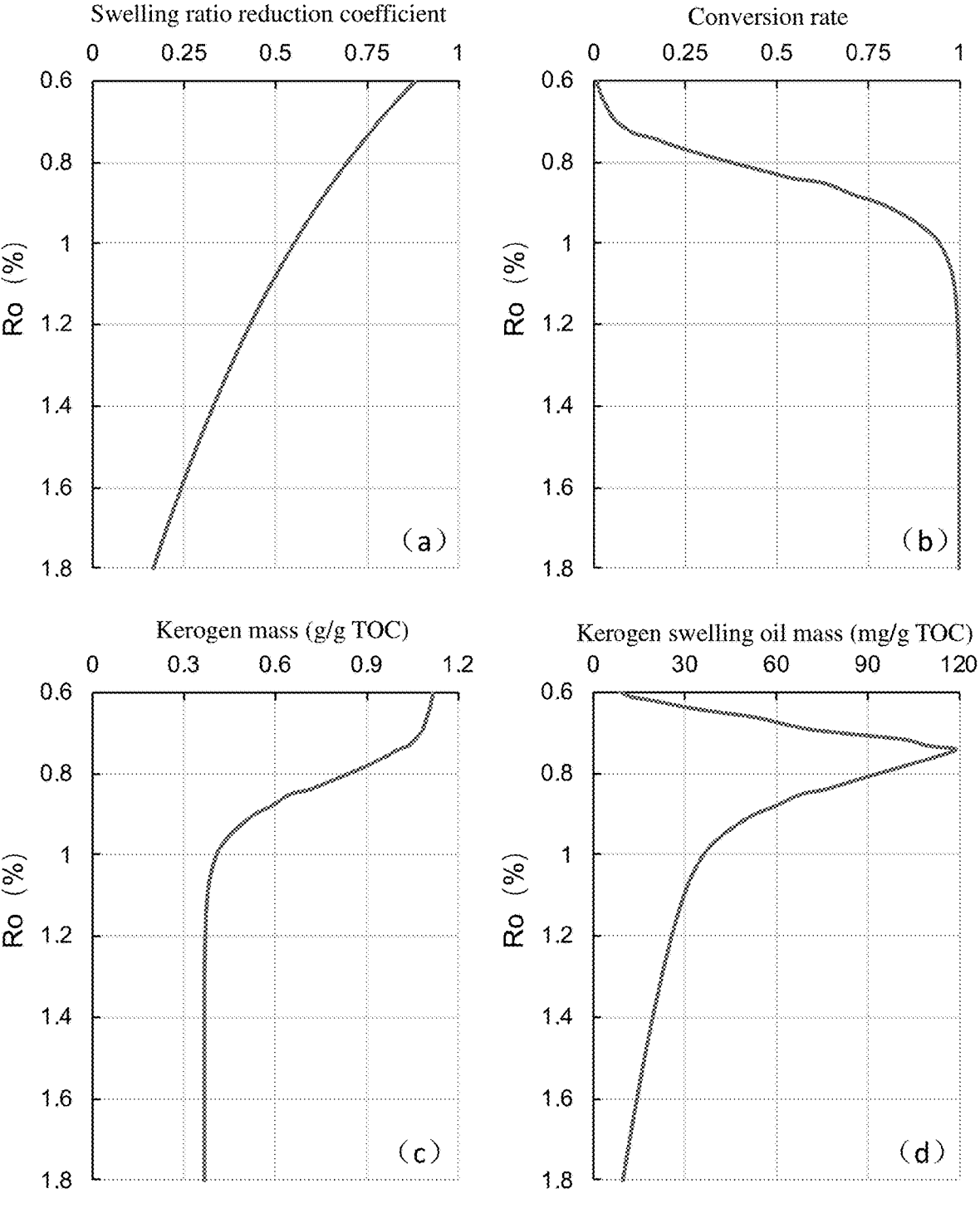
FIG. 6 shows a parameter necessary for a quantitative calculation process of kerogen swelling oil and a calculation result according to the present invention.

FIG. 6 shows a parameter necessary for a quantitative calculation process of kerogen swelling oil and a calculation result according to the present invention. Taking the kerogen swelling oil mass of the Qing-1 Member in the Songliao Basin as an example, as the shale in the Qing-1 Member is dominated by the type I kerogen, a swelling oil mass in the type I kerogen derived by a molecular dynamics simulation was used as an initial swelling mass. The ability of the oil to swell the kerogen decreases continuously with the evolution stage. 1 g of original organic carbon was used to normalize the kerogen swelling oil mass. The initial swelling mass multiplied by the mass of the type I kerogen in different evolution stages and by the swelling ratio reduction coefficient (FIG. 6a) to obtain the swelling oil mass in the type I kerogen in different evolution stages.

Swelling mass in the type I kerogen in different evolution stages:

$$Q_s=Q_w\cdot m_k\cdot f_s$$

In the formula, $Q_w$ is the swelling oil mass in the type I kerogen, 161.04 mg/g; $m_k$ is the kerogen mass in different evolution stages; $f_s$ is the swelling ratio reduction coefficient in different evolution stages, dimensionless.

Kerogen mass corresponding to 1 g of original organic carbon:

$$m_k=m_f F_t+m_s=(HI^0/1000)\cdot F_t+(1-HI^0\cdot 0.083/100) \tag{3}$$

In the formula, $m_f$ is the mass of a convertible part of the kerogen, g; $m_s$ is the mass of a non-convertible part of the kerogen, g; $HI^0$ is an original hydrogen index, mg/g TOC; 0.083 is a carbon conversion coefficient of the hydrogen index, dimensionless; $F_t$ is a conversion rate, dimensionless. The $HI^0$ of the type I kerogen in the shale of the Qing-1 Member in the north of the Songliao Basin was determined as 750 mg/g TOC according to the geochemical data thereof.

Taking the shale of the Qing-1 Member in the north of the Songliao Basin as an example, a chemical kinetics parameter of the primary cracking of the kerogen was calibrated based on a pyrolysis gas chromatography (PY-GC) test result of an immature shale sample of the Qing-1 Member in the Du 402 well in the Taikang uplift in the north of the Songliao Basin, as well as the principles of chemical kinetics. Based on the burial history and thermal history of the Songliao Basin, the conversion rates corresponding to different $R_o$ were calculated (FIG. 6b), and the kerogen mass and kerogen swelling oil mass in different evolution stages were calculated according to Formulas 2 and 3 (FIGS. 6c and 6d).

Steps 101-106 of the present invention used a real kerogen model, which overcame the problems caused by the conventional method of using simple graphene instead of kerogen to study the kerogen-shale oil interaction. As graphene is a two-dimensional carbon material with a smooth surface and a surface structure different from kerogen molecules, the shale oil molecules cannot pass through the graphene and enter its lamellar structure to make the graphene swell like the real kerogen structure. The kerogen aggregate model was preprocessed to prevent incomplete compaction of a kerogen aggregate. If the kerogen aggregate was incompletely compacted, it would result in the existence of "large pores" inside, making the density of the kerogen aggregate model lower than that of the kerogen sample.

In steps 107-109 of the present invention, the processing of the per-unit swelling oil mass overcame the problem that a molecular dynamics simulation system is too small to be applied to the swelling shale oil. A shale oil-kerogen system used for molecular dynamics simulation is usually less than 20 nm, while the pore size of most shale reservoirs is greater than 20 nm. The present invention calculated the per-unit kerogen swelling oil mass, and calculated the actual kerogen swelling oil mass based on actual geological parameters such as swelling coefficient reduction and kerogen mass change, which greatly improved the accuracy of the results.

The present invention further provides a system for quantitatively evaluating kerogen swelling oil in shale. FIG. 7 is a structural diagram of a system for quantitatively evaluating kerogen swelling oil in shale according to the present invention. As shown FIG. 7, a system for quantitatively evaluating kerogen swelling oil in shale includes:

a first initial model establishment module 201, for establishing different types of kerogen molecular models, and loading each of the kerogen molecular models into a graphene slit-type pore composed of a lamellar structure to obtain an initial model;

a compaction model 202, for subjecting each initial model to EM and relaxation to obtain a compacted kerogen aggregate model;

an annealing model 203, for simulating an annealing process of the compacted kerogen aggregate model to obtain a kerogen slit-type pore;

a second initial model establishment module 204, for loading a shale oil molecule into the kerogen slit-type pore to obtain an initial model of swelling and adsorption of shale oil in kerogen;

an assigning module 205, for assigning a value to a force field of the shale oil molecule and the kerogen molecule in the initial model of swelling and adsorption of the shale oil in the kerogen to obtain a density of the kerogen and the shale oil;

a density curve plotting module 206, for plotting a density curve of the kerogen and the shale oil according to the density of the kerogen and the shale oil;

a kerogen swelling oil mass determination module 207, for deriving the kerogen swelling oil mass according to the density curve of the kerogen and the shale oil;

a per-unit kerogen swelling oil mass determination module 208, for determining per-unit kerogen swelling oil mass according to the kerogen swelling oil mass; and a different-evolution-stage kerogen swelling oil mass determination module 209, for determining the kerogen swelling oil mass in different evolution stages according to the per-unit kerogen swelling oil mass.

The compaction module 202 specifically includes:

a compaction unit, for subjecting the initial model to EM and 200 ps relaxation at 75° C. under 20 MPa by using Gromacs software to obtain a compacted kerogen aggregate model.

The annealing module 203 specifically includes:

a warming unit, for subjecting the compacted kerogen aggregate model to 200 ps relaxation for warming; and an annealing unit, for subjecting the kerogen aggregate model after the relaxation warming to 2 ns simulation, cooling and pressurization by using a NPT ensemble at 800° C. under normal pressure to obtain a kerogen slit-type pore.

The kerogen swelling oil mass determination module 207 specifically includes:

a kerogen swelling oil mass determination unit, for deriving the kerogen swelling oil mass by $$Q_{oil} = \int_{L_{o1}}^{L_{o2}} S_{model} \cdot \rho_{oil} dL$$

according to the density curve of the kerogen and the shale oil.

In the formula, $Q_{oil}$ is the kerogen swelling oil mass; $L_{o1}$ is a start position of an intersection between the kerogen density curve and the shale oil density curve; $L_{o2}$ is a stop position of the intersection between the kerogen density curve and the shale oil density curve; $S_{model}$ is a cross-sectional area of the swelling and adsorption model of the shale oil in the kerogen; $\rho_{oil}$ is the shale oil density curve.

Each example of the present specification is described in a progressive manner, each example focuses on the difference from other examples, and the same and similar parts between the examples may refer to each other. For a system disclosed in the examples, since it corresponds to the method disclosed in the examples, the description is relatively simple, and reference can be made to the method description.

In this paper, several examples are used for illustration of the principles and implementations of the present invention. The description of the foregoing examples is used to help illustrate the method of the present invention and the core principles thereof. In addition, those of ordinary skill in the art can make various modifications in terms of specific implementations and scope of application in accordance with the teachings of the present invention. In conclusion, the content of this specification should not be construed as a limitation to the present invention.

What is claimed is:

1. A method for quantitatively evaluating kerogen swelling oil in shale, comprising:

establishing, by a molecular modeling software, different types of kerogen molecular models;

loading each of the kerogen molecular models into a graphene slit-type pore composed of a lamellar structure to obtain an initial model;

subjecting each initial model to energy minimization (EM) and relaxation to obtain a compacted kerogen aggregate model, comprising:

subjecting the initial model to EM and 200 ps relaxation at 75° C. under 20 MPa by using a molecular dynamics software to obtain a compacted kerogen aggregate model;

simulating an annealing process of the compacted kerogen aggregate model to obtain a kerogen slit-type pore, comprising:

subjecting the compacted kerogen aggregate model to 200 ps relaxation for warming; and subjecting the kerogen aggregate model, after the relaxation warming, to 2 ns simulation, cooling and pressurization by using an isothermal-isobaric ensemble (NPT ensemble) at 800° C. under normal pressure to obtain the kerogen slit-type pore;

loading shale oil molecules into the kerogen slit-type pore to obtain an initial model of swelling and adsorption of shale oil in kerogen;

assigning a value to a force field of the shale oil molecules and kerogen molecules in the initial model of swelling and adsorption of the shale oil in the kerogen to obtain a density of the kerogen and the shale oil;

plotting a density curve of the kerogen and the shale oil according to the density of the kerogen and the shale oil;

calculating kerogen swelling oil mass according to the density curve of the kerogen and the shale oil, comprising:

calculating the kerogen swelling oil mass by $$Q_{oil} = \int_{L_{o1}}^{L_{o2}} S_{model} \cdot \rho_{oil} dL$$

according to the density curve of the kerogen and the shale oil, where $Q_{oil}$ is the kerogen swelling oil mass; $L_{o1}$ is a start position of an intersection between the kerogen density curve and the shale oil density curve; $L_{o2}$ is a stop position of the intersection between the kerogen density curve and the shale oil density curve; $S_{model}$ is a cross-sectional area of the swelling and adsorption model of the shale oil in the kerogen; $\rho_{oil}$ is the shale oil density curve;

determining per-unit kerogen swelling oil mass according to the kerogen swelling oil mass;

determining the kerogen swelling oil mass in different evolution stages according to the per-unit kerogen swelling oil mass, comprising:

deriving kerogen mass $m_x$ in different evolution stages;

calculating the kerogen swelling oil mass in different evolution stages by $$Q_s = Q_w \cdot m_k \cdot f_s \qquad 5$$

according to the per-unit kerogen swelling oil mass $Q_w$ and the kerogen mass $m_k$ in different evolution stages;

where $Q_w$ is the kerogen swelling oil mass, $m_k$ is the kerogen mass in different evolution stages, $f_s$ is a swelling ratio reduction coefficient in different evolution stages, and $$m_k = m_f \cdot F_t + m_s = \left(HI^0 / 1000\right) \cdot F_t + \left(1 - HI^0 \cdot 0.083 / 100\right), \qquad 15$$

where $m_f$ is a mass of a convertible part of the kerogen, with a unit of g; $m_s$ is a mass of a non-convertible part of the kerogen, with a unit of g; $HI^0$ is an original hydrogen index, with a unit of mg/g TOC; 0.083 is a carbon conversion coefficient of the original hydrogen index, dimensionless; $F_t$ is a conversion rate, dimensionless;

carrying out a pyrolysis gas chromatography (PY-GC) test on an immature shale sample from a target region, and calibrating chemical kinetics parameters of a primary cracking of kerogen in the target region based on results of the pyrolysis gas chromatography test and principles of chemical kinetics so as to determine a conversion rate $F_t$ of the target region according to a burial history and thermal history of the target region;

determining an original hydrogen index $HI^0$ of the target region according to geochemical data of the target region; and obtaining a type of kerogen, a kerogen mass and a current evolution stage of the target region to determine a kerogen swelling oil mass in the target region based on the conversion rate and the original hydrogen index of the target region.

2. The method according to claim 1, wherein the determining per-unit kerogen swelling oil mass according to the kerogen swelling oil mass comprises:

deriving the mass of the kerogen; and determining the per-unit kerogen swelling oil mass according to the kerogen adsorbed oil mass and the kerogen mass.

* * * * *